(12) United States Patent
Holmes et al.

(10) Patent No.: US 7,358,398 B2
(45) Date of Patent: Apr. 15, 2008

(54) METHODS OF AMINATION

(75) Inventors: Andrew Bruce Holmes, Melbourne (AU); Catherine Janet Smith, Cambridge (GB); Melanie Wing-Sze Tsang, Putney (GB); Theresa Rachel Early, Cambridge (GB); Richard Eden Shute, Macclesfield (GB)

(73) Assignee: AstraZeneca UK Limited (GB)

( * ) Notice: Subject to any disclaimer, the term of this patent is extended or adjusted under 35 U.S.C. 154(b) by 0 days.

(21) Appl. No.: 10/593,212

(22) PCT Filed: Mar. 18, 2005

(86) PCT No.: PCT/GB2005/001130

§ 371 (c)(1),
(2), (4) Date: Feb. 23, 2007

(87) PCT Pub. No.: WO2005/090283

PCT Pub. Date: Sep. 29, 2005

(65) Prior Publication Data

US 2007/0179315 A1 Aug. 2, 2007

(30) Foreign Application Priority Data

Mar. 18, 2004 (GB) .................................. 0406125.5

(51) Int. Cl.
*C07C 209/00* (2006.01)
(52) U.S. Cl. ........................................................ 564/386
(58) Field of Classification Search .................... None
See application file for complete search history.

(56) References Cited

U.S. PATENT DOCUMENTS

| 5,576,460 A | 11/1996 | Buchwald et al. |
| 6,156,933 A | 12/2000 | Poliakoff et al. |

FOREIGN PATENT DOCUMENTS

| EP | 0652202 | 5/1995 |
| WO | WO 94/06738 | 3/1994 |
| WO | WO 94/20444 | 9/1994 |
| WO | WO 95/22591 | 8/1995 |
| WO | WO 96/01304 | 1/1996 |
| WO | WO 02/28983 | 4/2002 |
| WO | WO 02/45868 | 6/2002 |
| WO | WO 02/051958 | 7/2002 |
| WO | WO 03/009936 | 2/2003 |
| WO | WO 03/018531 | 3/2003 |

OTHER PUBLICATIONS

Aalten, H.L. et al., "The copper catalysed reaction of sodium methoxide with aryl bromices. A mechanistic study leading to a facile synthesis of anisole derivatives," Tetrahedron (1989) 45(17):5565-5578.

Bae, Y.C. et al., "Tailoring transparency of imageable fluoropolymers at 157nm by incorporation of hexafluoroisopropyl alcohol to photoresist backbones," Chem. Mater. (2002) 14:1306-1313.

Baiker, A., "Supercritical fluids in heterogeneous catalysis," Chem. Rev. (1999) 99:453-473.

Carroll, M.A. et al., "Palladium-catalysed carbon-carbon bond formation in supercritical carbon dioxide," Chem. Commun. (1998) 1395-1396.

Cooper, A.I., "Recent developments in materials synthesis and processing using supercritical CO2," Adv. Mater. (2001) 13:1111-1114.

Deagostino, A. et al., "Palladium-catalyzed heck reaction on 1-alkoxy-1,3-dienes: a regioselective γ-arylation of α,β-unsaturated carbonyl compounds," Org. Lett. (2003) 5(21):3815-3817.

Early, T.R. et al., "Palladium-catalysed cross-coupling reactions in supercritical carbon dioxide," Chem. Commun. (2001) 1966-1967.

Furstner, A. et al., "Olefin metathesis in supercritical carbon dioxide," J. Am. Chem. Soc. (2001) 123:9000-9006.

Gordon, R.S. et al., "Palladium-mediated cross-coupling reactions with supported reagents in supercritical carbon dioxide," Chem. Commun. (2002) 640-641.

Halls, J.J.M. et al., "Efficient photodiodes from interpenetrating polymer networks," Nature (1995) 376:498-500.

Hartwig, J.F., "Transition metal catalyzed synthesis of arylamines and aryl ethers from aryl halides and triflates: scope and mechanism," Angew. Chem. Int. Ed. (1998) 37:2046-2067.

(Continued)

*Primary Examiner*—Samuel Barts
(74) *Attorney, Agent, or Firm*—Curatolo Sidoti Co., LPA; Salvatore A. Sidoti

(57) ABSTRACT

A method of synthesizing a compound of formula I: comprising the step of reacting a moiety of formula II: with a moiety of formula III: in compressed carbon dioxide in the presence of a transition metal catalyst and a base, wherein L is a labile leaving group; $R^{N1}$ is optionally substituted $C_{5-20}$ aryl; $R^{N2}$ is selected from optionally substituted $C_{5-20}$aryl, optionally substituted $C_{3-20}$ heterocyclyl, optionally substituted $C_{3-7}$ alkyl, and optionally substituted sulfonyl; $R^{N3}$ is selected from H and optionally substituted $C_{1-7}$ alkyl, $C_{3-20}$ heterocyclyl and $C_{5-20}$ aryl; or $R^{N2}$ and $R^{N3}$ together with the nitrogen atom to which they are attached form optionally substituted nitrogen-containing $C_{3-20}$ heterocylyl or $C_{5-20}$ heteroaryl; and $R^1$ $R^2$ and $R^3$ are independently selected from optionally substituted $C_{1-7}$ alkyl, $C_{5-20}$ aryl, $C_{3-20}$ heterocyclyl, hydroxy, halo, amino and $C_{1-7}$ alkoxy, or two of $R^1$, $R^2$ and $R^3$, together with the silicon atom to which they are attached, may form a silicon containing $C_{5-7}$ heterocyclyl group.

(I)

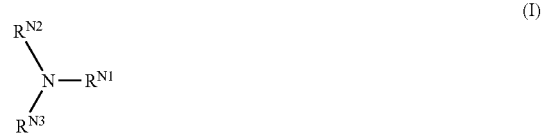

13 Claims, No Drawings

OTHER PUBLICATIONS

Hoggan, E.N. et al., "Spin coating and photolithography using liquid and supercritical carbon dioxide," Polym. Prep. Am. Chem. Soc. Div. PMSE (1999) 81:218.

Jessop, P.G. et al., Chemical Synthesis Using Supercritical Fluids, Wiley-VCH: Weinheim (1999).

Kissling, R.M. et al., "Recent developments in the use of N-heterocyclic carbenes: applications in catalysis," (2003) Chapter 27, 323-341.

Kitani, A. et al., "'Polyaniline': formation reaction and structure," Synthetic Metals (1987) 18:341-346.

Kuwabara, Y. et al., "Thermally stable multilayered organic electroluminescent devices using novel starburst molecules, 4,4',40"-tri(N-carbazolyl)triphenylamine (TCTA) and 4,4',4"-Tris(3-methylphenylphenyl-amino)triphenylamine (m-MTDATA), as hole-transport materials," Adv. Mater. (1994) 6(9):677.

Ley, S.V. et al., "Polyurea-encapsulated palladium(II) acetate: a robust and recyclable catalyst for use in conventional and supercritical media," Chem. Commun. (2002) 1134-1135.

Lindley, J., "Copper assisted nucleophilic substitution of aryl halogen," Tetrahedron (1984) 40(9):1433-1456.

Lu, F.-L. et al., "Phenyl-capped octaaniline (COA): an excellent model for polyaniline," J. Am. Chem. Soc. (1986) 108:8311-8313.

MacDiarmid, A.G. et al., "Polyaniline: a new concept in conducting polymers," Synthetic Metals (1987) 18:285-290.

MacDiarmid, A.G. et al., "Polyanilines: a novel class of conducting polymers," Faraday Discuss. Chem. Soc. (1989) 88:317-332.

MacDiarmid, A.G. et al., "The polyanilines: potential technology based on new chemistry and new properties," Science and Applications of Conducting Polymers; Hilger: New York (1991) 117-127.

Oakes, R.S. et al., "The use of supercritical fluids in synthetic organic chemistry," J. Chem. Soc. Perkin Trans. (2001) 1:917-941.

Paine, A.J., "Mechanisms and models for copper mediated nucleophilic aromatic substitution. 2. A single catalytic species from three different oxidation states of copper in an Ullmann synthesis of triarylamines," J. Am. Chem. Soc. (1987) 109:1496-1502.

Ray, A. et al., "Polyaniline: doping, structure and derivatives," Synthetic Metals. (1989) 29:E141-E150.

Shezad, N. et al., "Pd-catalysed coupling reactions in supercritical carbon dioxide and under solventless conditions," Green Chem. (2002) 4:64-67.

Shezad, N. et al., "Pd-catalyzed coupling reactions in supercritical carbon dioxide," Chemical Industries (Dekker) (2001) 82:459-464.

Smith, C.J. et al., "Palladium catalysed aryl amination reactions in supercritical carbon dioxide," Org. Biomol. Chem. (2005) 3:3767-3781.

Smith, C.J. et al., "Palladium catalyzed cross-coupling reactions of silylamines," Chem. Commun. (2004) 1976-1977, Jul. 2004.

Stolka, M. et al., "Hole transport in solid solutions of a diamine in polycarbonate," J. Phys. Chem. (1984) 88:4707-4714.

Strukelj, M. et al., "Organic multilayer white light emitting diodes," J. Am. Chem. Soc. (1996) 118:1213-1214.

Sundararajan, N. et al., "Supercritical $CO_2$ processing for submicron imaging of fluoropolymers," Chem. Mater. (2000) 12:41-48.

Tamao, K. et al., "Introduction to cross-coupling reactions," Topics in Curr. Chem. (2002) 219:1-9.

Ueta, E. et al., "Glass formation and phase transition of novel π-electron starburst molecules, 1,3,5-tris(phenyl-2-thienylamino)benzene and 1,3,5-tris(phenyl-3-thienylamino)benzene," Chem. Lett. (1994) 2397-2400.

Vachon, D. et al., "Polyaniline is poly-para-phenyleneamineimine: proof of structure by synthesis," Synthetic Metals (1987) 18:297-302.

Weingarten, H., "Ullmann condensation," J. Org. Chem. (1964) 29:975-977.

Wells, S.L. et al., "CO2 technology platform: an important tool for environmental problem solving," Angew. Chem. Int. Ed. (2001) 40:518-527.

Wolfe, J.P. et al., "Rational development of practical catalysts for aromatic carbon—nitrogen bond formation," Accounts of Chem. Res. (1998) 31(12):805-818.

Yang, B.H. et al., "Palladium-catalyzed amination of aryl halides and sulfonates," J. Organometallic Chem. (1999) 576:125-146.

METHODS OF AMINATION

CROSS-REFERENCE TO RELATED APPLICATIONS

This patent application is a national stage filing under 35 U.S.C. 371 of International Application No. PCT/GB2005/001130, filed on Mar. 18, 2005, which claims foreign priority benefits to United Kingdom Application No. 0406125.5, filed Mar. 18, 2004.

The present invention relates to methods of amination, and in particular to methods of aminating aromatic groups using transition metal catalysis.

Amine derivatives are exceptionally important pharmaceutical intermediates and active ingredients in many drugs. Aromatic amines form the basis of the modern organic-based photoconductors in xerography (photocopiers and photoconductors) [References 1-4], solar cells and as hole transporting materials in organic and polymeric light emitting devices [References 5-11].

Supercritical carbon dioxide and compressed carbon dioxide have emerged as a general environmentally benign solvent for the synthesis of organic molecules [References 12 and 13] and polymers [Reference 14]. It can be particularly beneficial in a variety of palladium-mediated syntheses and cross coupling reactions [References 15-18] and for the integration of synthesis with processing. Particular examples of use in organic electronic materials are described by Ober and DeSimone [References 19-22]. Opportunities for the controlled deposition of organic and polymeric electronic materials have been disclosed [Reference 23]. Deposition from compressed $CO_2$ will allow the controlled supramolecular ordering of materials owing to the ability to control demixing of samples during deposition from $CO_2$ solutions.

Amination reactions have been historically developed using the Ullmann coupling procedure [References 24 to 27], which involves the copper-mediated coupling of aryl halides and aryl 4-toluenesulfonates. More recently a family of palladium catalysed aromatic amination reactions have been developed in which an aryl halide or aryl tosylate is typically coupled with an amine derivative in the presence of a palladium (0) catalyst, a suitable bulky organophosphine ligand and a base [Reference 28]. The scope and methodology of such a procedure (the 'Buchwald-Hartwig' amination reaction) has been reviewed by Buchwald and Hartwig [References 29-31] and forms the basis of a wide variety of amine syntheses. The use of these methods for the manufacture of electroactive polymers has been described [Reference 32].

There is an attraction in combining the synthesis of aminederivatives and the subsequent processing in compressed $CO_2$. Advantages could include an environmentally friendly manufacturing process plus control of morphology of the final product using anti-solvent techniques (see A. I. Cooper's review [Reference 14]) for pharmaceuticals. In the electroactive organic and polymeric materials arena an advantage of integrated synthesis and processing will lead to architecturally controlled multilayered devices with supramolecular order. A particular example is the use of blended materials to improve organic LED device performance [Reference 33]. Another example of the benefit of an integrated synthesis and processing system is the advantage of polymer deposition where layer separation is required, by virtue of the immiscibility of the deposition solvent with the first layer, or induction of microphase segregation of two materials co-deposited from carbon dioxide whose solubility difference can be exploited to generate organised and phase segregated materials. This feature has specific advantages in organic photovoltaic devices [Reference 34].

Although palladium catalysed carbon-carbon bond formation reactions in supercritical $CO_2$ have been described [Reference 36], prior art in the field would suggest that carrying out the palladium catalysed amination reaction in compressed $CO_2$ (the Buchwald-Hartwig amination reaction) would fail because it is well known that amines form carbamic acids in the presence of carbon dioxide. In fact, the formation of a carbamic acid has been used to suppress the reactivity of a free amino substituent in the course of a synthesis in compressed carbon dioxide [Reference 35].

The present inventors have now discovered that palladium catalysed amination reactions can be carried in compressed $CO_2$ by the use of selected N-silylamines.

Accordingly, the present invention provides a method of synthesizing a compound of formula I:

comprising the step of reacting a moiety of formula II:

with a moiety of formula III:

in compressed carbon dioxide in the presence of a transition metal catalyst and a base, wherein:

L is a labile leaving group;

$R^{N1}$ is optionally substituted $C_{5-20}$ aryl;

$R^{N2}$ is selected from optionally substituted $C_{5-20}$ aryl, optionally substituted $C_{3-20}$ heterocyclyl, optionally substituted $C_{3-7}$ alkyl, and optionally substituted sulfonyl;

$R^{N3}$ is selected from H and optionally substituted $C_{1-7}$ alkyl, $C_{3-20}$ heterocyclyl and $C_{5-20}$ aryl; or $R^{N2}$ and $R^{N3}$ together with the nitrogen atom to which they are attached form optionally substituted nitrogen-containing $C_{3-20}$ heterocylyl or $C_{5-20}$ heteroaryl; and $R^1$, $R^2$ and $R^3$ are independently selected from optionally substituted $C_{1-7}$ alkyl, $C_{5-20}$ aryl, $C_{3-20}$ heterocyclyl, hydroxy, halo, amino and $C_{1-7}$ alkoxy, or two of $R^1$, $R^2$ and $R^3$, together with the silicon atom to which they are attached, may form a silicon containing $C_{5-7}$ heterocyclyl group (e.g. silacyclobutyl).

$R^{N1}$ and $R^{N2}$ may be linked by a single bond, such that the compound of formula I comprises a nitrogen-containing $C_{5-7}$ heterocyclyl or heteroaryl group formed from $R^{N1}$ and $R^{N2}$, and the nitrogen to which they are attached.

It has also been found that these reactions proceed more efficiently than when carried out in an organic solvent, such as toluene.

Compressed Carbon Dioxide

The term "compressed carbon dioxide" means herein carbon dioxide which has been compressed under pressure to produce liquid carbon dioxide or supercritical or near supercritical carbon dioxide.

A fluid is termed "supercritical" when its temperature exceeds the critical temperature (Tc). At this point the two fluid phases, liquid and vapor, become indistinguishable [Reference 37]. The critical temperature of carbon dioxide is 31.1° C. and the critical pressure 73.8 bar. Conditions and solvent media required to form supercritical or near supercritical states are described in Reference 12 and References 38 to 45.

The reaction is preferably carried out at a pressure between 800 psi and 4000 psi. More preferably the reaction pressure is greater than, or equal to, 1500 psi. The reaction is also more preferably less than, or equal to, 3500 psi.

Transition Metal Catalyst

Suitable transition metal catalysts include complexes of platinum, palladium, iron, nickel, ruthenium and rhodium. Catalyst complexes may include chelating ligands, such as, by way of example only, $C_{1-7}$ alkyl and $C_{5-20}$ aryl derivatives of phosphiones and bisphosphines, imines, arsines and hybrids thereof, including hybrids of phosphines with amines.

Additionally, heterogeneous catalysts containing forms of these elements are also suitable as catalysts for the present invention. Catalysts containing palladium and copper are preferred, with palladium based catalysts being more preferred.

The active form of the transition metal catalyst is not well characterised. Therefore, the term "transition metal catalyst" as used herein refers to any transition metal catalyst and/or catalyst precursor as is introduced into the reaction vessel and which is, if necessary, converted into the active phase, as well as active form, of the catalyst which participates in the reaction.

The palladium catalysts most suitable for use in the present invention are formed from palladium(II) salts and appropriate ligands, preferably phosphine ligands. Such catalysts are known in the art and are described in Reference 12, 36, 38-45. Particularly preferred catalysts include Pd catalysts with one or more phosphine ligands such as $PPh_3$, $P(C_6H_{12})_3$, 2-diphenylphosphinophenol, binap, dppf, $P(t-Bu)_2(biphen)$ where biphen represents 2-phenyl-phen-1-yl, where the 2-phenyl group may bear at one or more of the 2',4' and 6'-positions iso-propyl groups or N,N-dimethyl amino groups. Examples of catalysts include, but are not limited to, those derived from Pd(II) acetate (especially with $P(t-Bu)_2(biphen)$ ligands, where biphen is as defined above), $Pd(PPh_3)_4$, $Pd(PPh_3)_2Cl_2$ and $Pd(dppf) Cl_2$.

Other preferred transition metal (preferably palladium) catalysts are those based on the N-heterocyclic carbenoid ligands described for example by Nolan [Reference 46], and the micro-encapsulated transition metal catalysts disclosed in Reference 36.

The transition metal catalyst is preferably present in the range of 0.001 to 20 mol %, and preferably 1.0 to 2.5 or 5 mol %, with respect to the moiety of formula II.

Base

Suitable bases for use in the present invention include bases of group 1 metals, carbonate, phosphate or tert-butoxy/phenoxy bases and superbases [References 47 and 48]. Preferred bases are group 1 metal carbonate, phosphate or tert-butoxy/phenoxy bases, such as $K_2CO_3$, $K_3PO_4$, $Na_2CO_3$, $Cs_2CO_3$, K(t-BuO), Na(t-BuO), K(OPh), Na(OPh), and tetraalkylammonium salts or mixtures thereof.

Preferred bases include $K_2CO_3$, $Na_2CO_3$ and $Cs_2CO_3$, of which $Cs_2CO_3$ is most preferred.

The base is preferably present as 1 to 4 equivalents of the moiety of formula II, and more preferably as 1 to 1.5 or 2 equivalents.

Optional Additive

The reaction mixture may also contain an optional additive which acts as a fluoride source, to aid the progress of the reaction. Such fluoride sources include, but are not limited to, KF, CsF, tetrabutylammonium fluoride, tris(diethylaminosulfonium difluorotrimethylsilicate (TASF) and tetrabutylammonium triphenyldifluorosilicate (TBAT), of which KF is most preferred.

The optional additive is preferably present as 1 to 2 equivalents of the moiety of formula III, and more preferably as 1 to 1.3 or 1.5 equivalents.

Labile Leaving Group

Labile leaving groups suitable for use in the present invention are in particular those known to be amenable to palladium catalysed coupling. Suitable groups include mesylate ($—OSO_2CH_3$); $—OSO_2(C_nF_{2n+1})$, where n=0-4; $—OSO_2—R^S$, where $R^S$ is an optionally substituted phenyl group (e.g. 4-Me-Ph, tosylate); $—N^+Me_3X^-$, where X may be OTf, OTs, I, Br, Cl, OH; I, Br and Cl. More preferred are $—OSO_2(C_nF_{2n+1})$ where n=0, 1 or 4 (in particular triflate), I, Br and Cl, with Br being the most preferred.

Amount of Compound of Formula III

When the moiety of formula III is not bound to the moiety of formula II, it is preferably present as 1 to 2 equivalents, and is more preferably 1 to 1.3 or 1.5 equivalents, of the compound of formula II.

Reaction Temperature

The reaction is preferably carried out at room temperature (i.e. 20° C.) or higher, more preferably higher than 50° C., but at 200° C. or lower. A most preferred temperature range for the reaction is between 60° C. and 120° C., with temperatures of about 100° C. being particularly preferred.

Substituents

The phrase "optionally substituted" as used herein, pertains to a parent group which may be unsubstituted or which may be substituted.

Unless otherwise specified, the term "substituted" as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below. $C_{1-7}$ alkyl: The term "$C_{1-7}$ alkyl" as used herein, pertains to a monovalent moiety obtained by removing a hydrogen atom from a carbon atom of a hydrocarbon compound having from 1 to 7 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$) hexyl ($C_6$) and heptyl ($C_7$)

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-7}$ Alkenyl: The term "$C_{2-7}$ alkenyl" as used herein, pertains to an alkyl group having one or more carbon-carbon double bonds.

Examples of unsaturated alkenyl groups include, but are not limited to, ethenyl (vinyl, —CH═$CH_2$), 1-propenyl (—CH═CH—$CH_3$), 2-propenyl (allyl, —CH—CH═$CH_2$), isopropenyl (1-methylvinyl, —C($CH_3$)═$CH_2$), butenyl ($C_4$), pentenyl ($C_5$), and hexenyl ($C_6$).

$C_{2-7}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (ethinyl, —C≡CH) and 2-propynyl (propargyl, —$CH_2$—C≡CH).

$C_{3-7}$ cycloalkyl: The term "$C_{3-7}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds: cyclopropane ($C_3$), cyclobutane ($C_4$), cyclopentane ($C_5$) cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds: norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$)

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH($OR^1$) ($OR^2$), wherein $R^1$ and $R^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe) (OEt).

Hemiacetal: —CH(OH) ($OR^1$), wherein $R^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH) (OMe) and —CH(OH) (OEt).

Ketal: —CR($OR^1$) ($OR^2$), where $R^1$ and $R^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of ketal groups include, but are not limited to, —C(Me) (OMe)$_2$, —C(Me) (OEt)$_2$, —C(Me) (OMe) (OEt), —C(Et) (OMe)$_2$, —C(Et) (OEt)$_2$, and —C(Et)(OMe) (OEt).

Hemiketal: —CR(OH) (OR$_1$), where $R^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me) (OH) (OMe), —C(Et) (OH) (OMe), —C(Me) (OH) (OEt), and —C(Et) (OH) (OEt).

Oxo (keto, -one): ═O.

Thione (thioketone): ═S.

Imino (imine): ═NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, ═NH, ═NMe, ═NEt, and ═NPh.

Formyl (carbaldehyde, carboxaldehyde): —C(═O)H.

Acyl (keto): —C(═O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(═O)CH$_3$ (acetyl), —C(═O)CH$_2$CH$_3$ (propionyl), —C(═O)C(CH$_3$)$_3$ (t-butyryl), and —C(═O)Ph (benzoyl, phenone).

Carboxy (carboxylic acid): —C(═O)OH.

Thiocarboxy (thiocarboxylic acid): —C(═S)SH.

Thiolocarboxy (thiolocarboxylic acid): —C(═O)SH.

Thionocarboxy (thionocarboxylic acid): —C(═S)OH.

Imidic acid: —C(═NH)OH.

Hydroxamic acid: —C(═NOH)OH.

Ester (carboxylate, carboxylic acid ester, oxycarbonyl): —C(═O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(═O)OCH$_3$, —C(═O)OCH$_2$CH$_3$, —C(═O)OC(CH$_3$)$_3$, and —C(═O)OPh.

Acyloxy (reverse ester): —OC(═O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(═O)CH$_3$ (acetoxy), —OC(═O)CH$_2$CH$_3$, —OC(═O)C(CH$_3$)$_3$, —OC(═O) Ph, and —OC(═O)CH$_2$Ph.

Oxycarboyloxy: —OC(═O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(═O)OCH$_3$, —OC(═O)OCH$_2$CH$_3$, —OC(═O)OC(CH$_3$)$_3$, and —OC(═O)OPh.

Amino: —NR$^1$R$^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$ aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

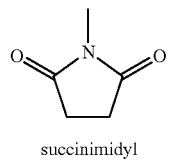

succinimidyl

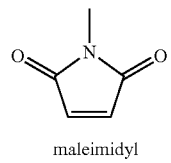

maleimidyl

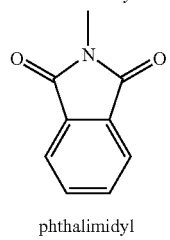

phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

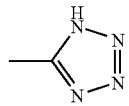

Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Disulfide: —SS—R, wherein R is a disulfide substituent, for example, a C$_{1-7}$ alkyl group, a C$_{3-20}$ heterocyclyl group, or a C$_{5-20}$ aryl group, preferably a C$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group, preferably a C$_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group, including, for example, a fluorinated or perfluorinated C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$ alkyl group, a C$_{3-20}$ heterocyclyl group, or a C$_{5-20}$aryl group, preferably a C$_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Further Substituent Groups

Particular substituent groups of interest are ion-chelating groups of formula [—(CH$_2$CH$_2$O)$_n$CH$_2$CH$_2$OCH$_3$], [—O(CH$_2$CH$_2$O)$_n$OCH$_3$], [—(CH$_2$CH(R$^4$)O)$_n$CH$_2$CH$_2$OCH$_3$] and [—O(CH$_2$CH(R$^4$)O)$_n$OCH$_3$], wherein n is an integer from 0 to 10, preferably 2 to 10, more preferably 2 to 4, and R$^4$ is C$_{1-10}$ alkyl, preferably C$_{1-2}$ alkyl, and wherein the ion chelating groups comprise side chains in ologomeric or polymeric structures.

The ion chelating side chains are based on the repeat unit [—OCH$_2$CH$_2$—]. Side chain branching and/or the inclusion of [—OCH$_2$O—] repeat-units, are advantageous to inhibit crystallisation after metal ion complexation. The side chains contain preferably 3 or more [—OCH$_2$CH$_2$—] and most preferably 3 units terminating in OR$^4$(R$^4$=C$_{1-10}$ alkyl, e.g. methyl) containing 4 oxygen atoms for cation chelation. Crown ethers may also be designed accordingly. Other side chain designs may be made according to the specific need for cation binding. Alternative design features could be incorporated into monomers and polymers to favour anion binding.

These substituent groups are discussed in detail in Reference 32.

The Ar¹, Ar² and Ar³ groups as defined in Reference 32 are also of interest as $R^{N1}$, $R^{N2}$ and $R^{N3}$ in the present invention.

Compounds of Formula II

These compounds are either commercially available, or may be readily synthesised using known techniques.

Compounds of Formula III

Compounds of formula III:

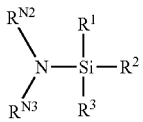

(III)

can be synthesised from compounds of Formula 1:

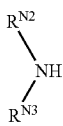

Formula 1 by methods known in the art. The method chosen will depend on the basicity of the amine of formula 1. Typically, the compound of formula 1 will be reacted with a base in organic solvent and then a compound of formula 2 added:

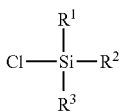

Formula 2

For example, some of the silylamines used in the examples below were prepared as follows from the free amine.

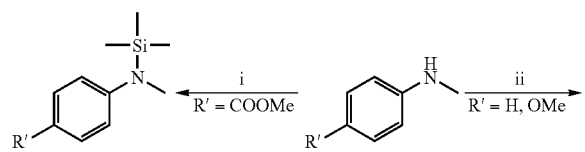

R' = COOMe, 67%

R' = H, 65%
R' = OMe, 73%

(i) TMSCl, NEt₃, CH₂Cl₂, 17 h
(ii) a. n-BuLi, THF, -78° C., 2 h. b. TMSCL, rt, 17 h

The silylamines where $R^{N2}$ is sulfonyl were prepared as follows from a modified amine by heating with bis(trimethylsilyl)trifluoroacetamide (BSTFA).

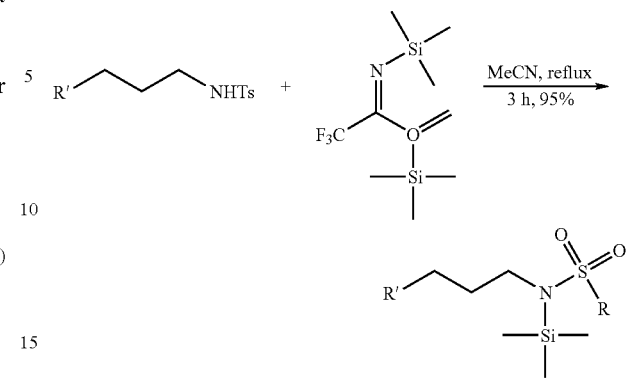

The silylamines were purified by vacuum distillation. Once purified, their were handled under nitrogen at all times, and stored at −20° C.

If the desired compound of formula I is a tri-aryl amine, then the bi-aryl silyl amine of formula III, may itself be synthesised from a bi-aryl amine made by the method of the present invention.

Further Preferences

The compounds of formula (I) may be oligomeric or polymeric in nature, as described in Reference 32. In particular, all of $R^{N1}$, $R^{N2}$ and $R^{N3}$ may be substituted $C_{5-20}$ aryl, preferably phenyl, with one of $R^{N1}$, $R^{N2}$ and $R^{N3}$ being a side chain group, and the other two of $R^{N1}$, $R^{N2}$ and $R^{N3}$ being linked to form an oligomeric or polymeric backbone.

In some embodiments $R^{N1}$ and $R^{N2}$ are not linked by a single bond.

$R^{N1}$ $R^{N1}$ is, in some embodiments, preferably optionally substituted $C_{5-7}$ aryl, more preferably optionally substituted phenyl.

$R^{N2}$ $R^{N2}$ is preferably selected from optionally substituted $C_{5-20}$ aryl, optionally substituted $C_{5-20}$ heterocyclyl, and optionally substituted sulfonyl. If $R^{N2}$ is a sulfonyl group, then the sulfonyl substituent is preferably optionally substituted $C_{1-7}$ alkyl.

$R^{N2}$ is more preferably selected from optionally substituted $C_{5-20}$ aryl and optionally substituted $C_{5-20}$ heterocyclyl, with optionally substituted $C_{5-20}$ aryl (e.g. phenyl) being most preferred.

$R^{N3}$ $R^{N3}$ is preferably selected from optionally substituted $C_{1-7}$ alkyl, $C_{3-20}$ heterocyclyl and $C_{5-20}$ aryl. If $R^{N3}$ is selected from $C_{1-7}$ alkyl, it is preferably $C_{1-4}$ alkyl, and most preferably methyl. If $R^{N3}$ is selected from $C_{5-20}$ aryl, it is preferably $C_{5-7}$ aryl, and most preferably phenyl.

$R^{N2}$ and $R^{N3}$

When $R^{N2}$ and $R^{N3}$ together with the nitrogen atom to which they are attached form optionally substituted nitrogen-containing $C_{3-20}$ heterocyclyl or $C_{5-20}$ heteroaryl, they preferably form optionally substituted nitrogen-containing $C_{5-20}$ heterocylyl or heteroaryl (e.g. pyrrolyl, indolyl).

$R^1$, $R^2$ and $R^3$ $R^1$, $R^2$ and $R^3$ are preferably independently selected from optionally substituted $C_{1-7}$ alkyl, $C_{5-20}$ aryl, $C_{3-2}$ heterocyclyl and $C_{1-7}$ alkoxy, or two of $R^1$, $R^2$ and $R^3$, together with the silicon atom to which they are attached, may form a silicon containing $C_{5-7}$ heterocyclyl group. It is more preferred that $R^1$, $R^2$ and $R^3$ are independently selected from optionally substituted $C_{1-7}$ alkyl, $C_{5-20}$ aryl and $C_{3-20}$ heterocyclyl, with optionally substituted $C_{1-7}$ alkyl being most preferred.

Examples of preferred $SiR^1R^2R^3$ groups include TMS, TES, TIPS, TDDMS, TBDPS and 1-methylsilacyclobutane.

Optional Substituents

The optional substituents for $R^{N1}$, $R^{N2}$ and $R^{N3}$ when they are $C_{5-20}$ aryl groups, for example phenyl, include, but are not limited to, $C_{1-7}$ alkyl, $C_{1-7}$ alkoxy and $C_{1-7}$ alkyl ester, of which, in some embodiments, $C_{1-7}$ alkoxy (e.g. OMe) and $C_{1-7}$ alkyl ester (e.g. COOMe) are preferred.

EXAMPLES

General Method

Flame dried cesium carbonate (228 mg, 0.7 mmol, 1.4 eq), aryl bromide (0.5 mmol), palladium acetate (2.8 mg, 0.012 mmol, 2.5 mol %) and di-tert-butyl biphenylphosphine (7.5 mg, 0.025 mmol, 5 mol %) were placed in a 10 cm³ stainless steal cell and the cell sealed. The cell was evacuated and refilled with nitrogen (three cycles). The silylamine (1.2 eq) was injected through the inlet port and the cell connected to the $CO_2$ line and charged with $CO_2$ (99.9995%—further purified over an Oxisor$^{RTM}$ catalyst) to approximately 760 psi (volume ca. 1 cm³ liquid carbon dioxide). The cell was heated to 100° C. and the pressure adjusted to the desired pressure by the addition of further $CO_2$. The reagents were maintained at this temperature and pressure for the desired time before the cell was allowed to cool to room temperature. The contents of the cell were vented into ethyl acetate (50 cm³), and once atmospheric pressure had been reached, the cell was opened and washed with further ethyl acetate (3×10 cm³). The combined organic fractions were filtered and concentrated in vacuo to furnish the crude material that was purified by flash column chromatography.

Example 1

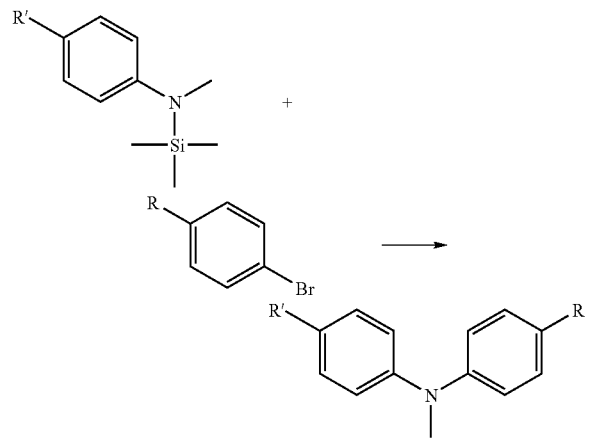

The reaction was carried out as described in the general method.

(a) R=COOMe, R'=COOMe, 3000 psi, 17 hours: Yield 84%
(b) R=COOMe, R'=COOMe, 1800 psi, 17 hours: Yield 69%
(c) R=COOMe, R'=OMe, 3000 psi, 17 hours: Yield 40%
(d) R=COOMe, R'=OMe, 1800 psi, 48 hours: Yield 77%
(e) R=COOMe, R'=H, 3000 psi, 17 hours: Yield 28%
(f) R=COOMe, R'=H, 1800 psi, 48 hours: Yield 76%
(g) R=H, R'=COOMe, 1800 psi, 17 hours: Yield 77%
(h) R=H, R'=H, 1800 psi, 48 hours: Yield 55%
(i) R=H, R'=OMe, 1800 psi, 48 hours: Yield 66%
(j) R=OMe, R'=COOMe, 1800 psi, 17 hours: Yield 57%
(k) R=OMe, R'=H, 1800 psi, 48 hours: Yield 25%
(l) R=OMe, R'=OMe, 1800 psi, 48 hours: Yield 25%

As a comparison, the reaction was carried out with the same reagents in toluene, as follows. To an oven dried Schlenk tube under nitrogen was added cesium carbonate (228 mg, 0.7 mmol, 1.4 eq) and the cesium carbonate was flame dried under vacuum with stirring. Methyl bromobenzoate (108 mg, 0.5 mmol), palladium acetate (5.6 mg, 0.024 mmol, 5 mol %) and di-tert-butyl biphenylphosphine (15 mg, 0.05 mmol, 10 mol %) were added and the Schlenk tube sealed, and evacuated and refilled with nitrogen (3 cycles). A solution of the silylamine (1.2 eq) in dry toluene (1.5 cm³) was added and the reaction mixture heated at 100° C. for the desired time. The reaction mixture was allowed to cool to room temperature. The mixture was filtered and concentrated in vacuo to furnish the crude material which was purified by flash column chromatography. The yields are shown in Table 1, with the time for each experiment in parentheses.

TABLE 1

|  | R=COOMe | R=H | R=OMe |
|---|---|---|---|
| R'=COOMe | 66 (34 h) | 41 (17 h) | 63 (17 h) |
| R'=H | 65 (54 h) | 12 (17 h) | 8 (17 h) |
| R'=OMe | 72 (54 h) | 25 (17 h) | 7 (17 h) |

Example 2

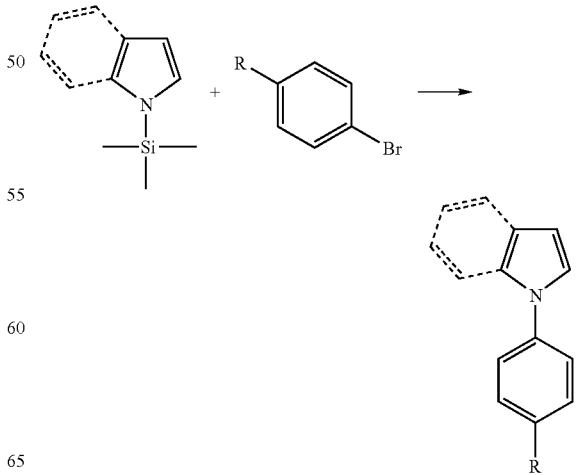

The reaction was carried out as described in the general method, with the R group and either the N-trimethylsilyl-pyrrole or indole as shown in Table 3, with the yields expressed in %. The reactions were carried out at ca. 1800 psi for 17 hours. The catalyst ligand used was either:

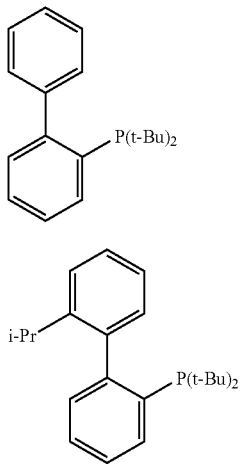

wherein ligand A is that described in the general method.

TABLE 2

| Substrate | X | Yield (%) A | Yield (%) B |
|---|---|---|---|
| Pyrrole | COOMe | 59 | 75 |
|  | H | 11 | 46 |
|  | OMe | 7 | 30 |
| Indole | COOMe | 70 | 88 |
|  | H | 68 | 70 |
|  | OMe | 25 | 50 |

Example 3

TABLE 3

| R | Additive | Time (hours) | Yield (%) |
|---|---|---|---|
| *-C6H4-CH3 | — | 17 | 43 |
| *-C6H4-CH3 | — | 41 | 61 |
| *-C6H4-CH3 | KF | 41 | 57 |
| —CH3 | — | 17 | 55 |
| —CH3 | — | 41 | 28 |
| —CH3 | KF | 17 | 72 |

As a comparison, the reaction was also carried out where the starting material did not bear the trimethyl silyl group, as shown in Table 4:

TABLE 4

| R | Additive | Time (hours) | Yield (%) |
|---|---|---|---|
| *-C6H4-CH3 | — | 17 | 20 |
| —CH3 | — | 17 | 22 |

Example 4

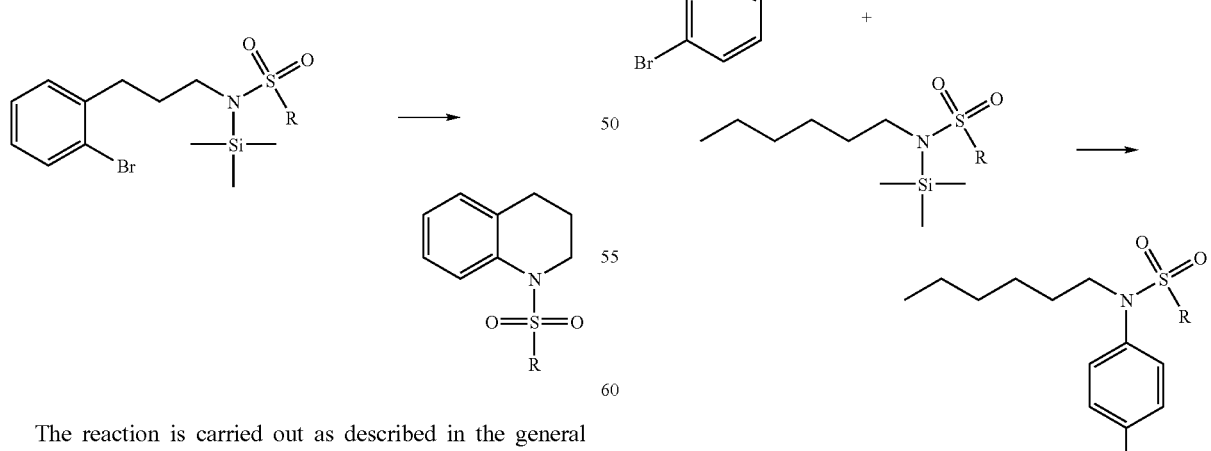

The reaction is carried out as described in the general method, wherein the starting material is added at the sily-lamine stage. An additive (1.2 eq) was sometimes added (see table 3) at the same time as the Cs₂CO₃. The reaction was carried out at 1800 psi for the length of time as shown in Table 3.

The reaction is carried out as described in the general method, and an additive (1.2 eq) was sometimes added (see table 5) at the same time as the $Cs_2CO_3$. The reaction was carried out at 1800 psi for the length of time as shown in Table 5.

TABLE 5

| R | R' | Additive | Time (hours) | Yield (%) |
|---|---|---|---|---|
| —$CH_3$ | COOMe | — | 17 | 15 |
| —$CH_3$ | COOMe | KF | 17 | 56 |
| —$CH_3$ | COOMe | KF | 41 | 55 |

REFERENCE (all of which Are Herein Incorporates by Reference)

(1) M. Stolka, J. F. Yanus, and D. M. Pai, *J. Phys. Chem.*, 1984, 88, 4707-4714

(2) E. Ueta, H. Nakano, and Y. Shirota, *Chem. Lett.*, 1994, 2397.

(3) Y. Kuwabara, H. Ogawa, H. Inada, N. Noma, and Y. Shirota, *Adv. Mater.*, 1994, 6, 677.

(4) M. Strukelj, R. H. Jordan, and A. Dodabalapur, *J. Am. Chem. Soc.*, 1996, 118, 1213-1214.

(5) A. Kitani, M. Kaya, J. Yano, K. Yoshikawa, and K. Sasaki, Synth. Met., 1987, 18, 341-346.

(6) F.-L. Lu, F. Wudl, M. Nowak, and A. J. Heeger, *J. Am. Chem. Soc.*, 1986, 108, 8311-13.

(7) A. G. MacDiarmid, J. C. Chiang, A. F. Richter, and A. J. Epstein, Synth. Met., 1987, 18, 285-290.

(8) A. G. MacDiarmid, and A. J. Epstein, Faraday *Discuss. Chem. Soc.*, 1989, 88, 317-332.

(9) A. G. MacDiarmid, and A. J. Epstein, *Science and Applications of Conducting Polymers;* Hilger: New York, 1991.

(10) A. Ray, A. F. Richter, D. L. Kershner, and A. J. Epstein, Synth. Met., 1989, 29, 141-150.

(11) D. Vachon, R. O. Angus, Jr., F.-L. Lu, M. Nowak, Z. X. Liu, H. Schaffer, F. Wudl, and A. J. Heeger, Synth. Met., 1987, 18, 297-302.

(12) R. S. Oakes, A. A. Clifford, and C. M. Rayner, *J. Chem. Soc. Perkin Trans* 1, 2001, 917-941.

(13) P. G. Jessop, and W. Leitner *Chemical Synthesis Using Supercritical Fluids;* Wiley-VCH: Weinheim, 1999.

(14) A. I. Cooper, *Adv. Mater.*, 2001, 13, 1111-1114.

(15) M. A. Carroll, and A. B. Holmes, *Chem. Commun.*, 1998, 1395-1396.

(16) T. R. Early, R. S. Gordon, M. A. Carroll, A. B. Holmes, R. E. Shute, and I. F. McConvey, *Chem. Commun.*, 2001, 1966-1967.

(17) R. S. Gordon, and A. B. Holmes, *Chem. Commun.*, 2002, 640-641.

(18) S. V. Ley, C. Ramarao, R. S. Gordon, A. B. Holmes, A. J. Morrison, I. F. McConvey, I. M. Shirley, S. C. Smith, and M. D. Smith, *Chem. Commun.*, 2002, 1134-1135.

(19) N. Sundararajan, S. Yang, K. Ogino, S. Valiyaveettil, J. G. Wang, X. Y. Zhou, C. K. Ober, S. K. Obendorf, and R. D. Allen, *Chem. Mater.*, 2000, 12, 41-48.

(20) Y. C. Bae, K. Douki, T. Y. Yu, J. Y. Dai, D. Schmaljohann, H. Koerner, C. K. Ober, and W. Conley, *Chem. Mater.*, 2002, 14, 1306-1313.

(21) J. M. D. E. Hoggan, R. G. Carbonell, *Polym. Prepr. Am. Chem. Soc. Div. PMSE,* Part 2 Aug. 22, 1999, 218.

(22) S. L. Wells, and J. DeSimone, *Angew. Chem. Int. Ed. Engl.,* 2001, 40, 518-527.

(23) F. Gaspar, T. Lu, R. Santos, B. Al-Duri, A. B. Holmes, G. Leeke, W. T. S. Huck, C. K. Luscombe, and J. Seville, Patterned deposition using compressed carbon dioxide, 2003, EP 1 341 616.

(24) J. Lindley, *Tetrahedron*, 1984, 40, 1433-1456.

(25) H. L. Aalten, G. van Koten, and D. M. Grove, *Tetrahedron*, 1989, 45, 5565-5578.

(26) A. J. Paine, *J. Am. Chem. Soc.,* 1987, 109, 1496-1502.

(27) H. Weingarten, *J. Org. Chem.,* 1964, 29, 975-977.

(28) S. L. Buchwald, and A. S. Guram, Preparation of arylamines, 1994, U.S. Pat. No. 5,576,460.

(29) J. P. Wolfe, S. Wagaw, J.-F. Marcoux, and S. L. Buchwald, *Acc. Chem. Res.,* 1998, 31, 805-818.

(30) J. F. Hartwig, *Angew. Chem. Int. Ed. Engl.,* 1998, 37, 2046-2047.

(31) B. Yang, and S. L. Buchwald, *J. Organometallic Chem.,* 1999, 576, 125-146; A. R. Muci and S. L. Buchwald in Topics in Current Chemistry: *Cross Coupling Reactions,* Vol. 219, Springer-Verlag, Berlin, 2002.

(32) A. B. Holmes, and T. Park, Electroactive polyarylamine-type compositions, 2002, WO 02/051958.

(33) C. Salvatore, Light emissive polymer blends and light emissive devices made from the same, 2003, EP 1 326 942.

(34) J. J. M. Halls, C. A. Walsh, N. C. Greenham, E. A. Marseglia, R. H. Friend, S. C. Moratti, and A. B. Holmes, *Nature,* 1995, 376, 498-500.

(35) A. Fürstner, L. Ackermann, K. Beck, H. Hori, D. Kock, K. Langermann, M. Liebl, C. Six, and W. Leitner, *J. Am. Chem. Soc.,* 2001, 123, 9000-9006.

(36) A. B. Holmes, R. S. Gordon, and T. R. Early, WO 03/009936.

(37) A. Baiker, Chem. Rev, 1999, 99, 453-474 (p. 455)

(38) Shezad, N., Oakes, R. S., Clifford, A. A., and Rayner, C. M., *Chemical Industries (Dekker)* 2001, 82 (Catalysis of Organic Reactions), 459-464

(39) N. Shezad, A. A. Clifford, and C. M. Rayner, *Green Chemistry* 2002, 4(1), 64-67

(40) WO96/01304

(41) WO95/22591

(42) WO94/20444

(43) WO94/06738

(44) EP 0 652 202

(45) U.S. Pat. No. 6,156,933

(46) Nolan, *Ionic liquids as green solvents: progress and prospects,* ACS Symposium Series, 2003, 856, 323-341

(47) A. Deagostino, C. Prandi and P. Venurello, *Org. Lett.,* 2003, 5, 3815-3817

(48) *New Aspects in Phosphorus Chemistry II, Top. Curr. Chem.,* 2003, 223, 1-44

The invention claimed is:

1. A method of synthesising a compound of formula I:

(I)

comprising the step of reacting a moiety of formula II:

(II)

with a moiety of formula III:

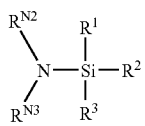

in compressed carbon dioxide in the presence of a transition metal catalyst and a base, wherein:
L is a labile leaving group;
$R^{N1}$ is optionally substituted $C_{5-20}$ aryl;
$R^{N2}$ is selected from optionally substituted $C_{5-20}$ aryl, optionally substituted $C_{3-20}$ heterocyclyl, optionally substituted $C_{3-7}$ alkyl, and optionally substituted sulfonyl;
$R^{N3}$ is selected from H and optionally substituted $C_{1-7}$ alkyl, $C_{3-20}$ heterocyclyl and $C_{5-20}$ aryl; or
$R^{N2}$ and $R^{N3}$ together with the nitrogen atom to which they are attached form optionally substituted nitrogen-containing $C_{3-20}$ heterocylyl or $C_{5-20}$ heteroaryl; and
$R^1$, $R^2$ and $R^3$ are independently selected from optionally substituted $C_{1-7}$ alkyl, $C_{5-20}$ aryl, $C_{3-20}$ heterocyclyl, hydroxy, halo, amino and $C_{1-7}$ alkoxy, or two of $R^1$, $R^2$ and $R^3$, together with the silicon atom to which they are attached, may form a silicon containing $C_{5-7}$ heterocyclyl group.

2. A method according to claim 1, wherein the compressed carbon dioxide is supercritical carbon dioxide.

3. A method according to claim 1, wherein the transition metal catalyst is a palladium catalyst.

4. A method according to claim 3, wherein the palladium catalyst comprises one or more phosphine ligands.

5. A method according to claim 1, wherein the base is selected from group 1 metal carbonate and tert-butoxy/phenoxy bases.

6. A method according to claim 5, wherein the base is $Cs_2CO_3$.

7. A method according to claim 1, wherein a fluoride source is present.

8. A method according to claim 7, wherein the fluoride source is selected from KF and CsF.

9. A method according to claim 1, wherein the reaction is carried out at a temperature of between 20 and 200° C.

10. A method according to claim 1, wherein the labile leaving group is selected from I, Br, Cl and $OSO_2CF_3$.

11. A method according to claim 1, wherein $R^{N2}$ is selected from optionally substituted $C_{5-20}$ aryl, optionally substituted $C_{5-20}$ heterocyclyl, and optionally substituted sulfonyl.

12. A method according to claim 1, wherein $R^{N3}$ is selected from optionally substituted $C_{1-7}$ alkyl, $C_{3-20}$ heterocylyl and $C_{5-20}$ aryl.

13. A method according to claim 1, wherein $R^1$, $R^2$ and $R^3$ are independently selected from optionally substituted $C_{1-7}$ alkyl, $C_{5-20}$ aryl, $C_{3-20}$ heterocyclyl and $C_{1-7}$ alkoxy, or two of $R^1$, $R^2$ and $R^3$, together with the silicon atom to which they are attached, may form a silicon containing $C_{5-7}$ heterocyclyl group.

* * * * *